(12) United States Patent
Shiflett et al.

(10) Patent No.: US 8,946,442 B2
(45) Date of Patent: Feb. 3, 2015

(54) FOAMED IONIC COMPOUNDS

(75) Inventors: Mark Brandon Shiflett, Wilmington, DE (US); Akimichi Yokozeki, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 774 days.

(21) Appl. No.: 12/974,006

(22) Filed: Dec. 21, 2010

(65) Prior Publication Data

US 2011/0319633 A1 Dec. 29, 2011

Related U.S. Application Data

(60) Provisional application No. 61/288,506, filed on Dec. 21, 2009, provisional application No. 61/288,510, filed on Dec. 21, 2009.

(51) Int. Cl.
| | |
|---|---|
| C07D 233/54 | (2006.01) |
| C07D 231/10 | (2006.01) |
| C07D 237/06 | (2006.01) |
| C07D 239/24 | (2006.01) |
| C07D 241/10 | (2006.01) |
| C07D 249/08 | (2006.01) |
| C07D 263/30 | (2006.01) |
| C07D 277/20 | (2006.01) |
| C07D 213/89 | (2006.01) |
| C07D 215/10 | (2006.01) |
| C07D 217/10 | (2006.01) |
| C07C 279/02 | (2006.01) |
| C07C 211/62 | (2006.01) |
| C07D 233/58 | (2006.01) |

(52) U.S. Cl.
CPC .................................... C07D 233/58 (2013.01)
USPC ........ 548/335.1; 544/139; 544/152; 544/179; 544/180; 544/224; 544/242; 544/336; 546/347; 548/146; 548/215; 548/262.2; 548/356.1; 562/8; 564/230; 564/281; 564/293

(58) Field of Classification Search
USPC ........ 548/335, 146, 215, 262.2, 335.1, 356.1; 546/347; 544/139, 152, 179, 180, 224, 544/242, 336; 562/8; 564/230, 281, 293
See application file for complete search history.

(56) References Cited

U.S. PATENT DOCUMENTS

| | | |
|---|---|---|
| 2004/0133058 A1 | 7/2004 | Arlt et al. |
| 2008/0028777 A1 | 2/2008 | Boesmann et al. |
| 2008/0073622 A1 | 3/2008 | Housel et al. |
| 2008/0319164 A1 | 12/2008 | Barreiros et al. |

FOREIGN PATENT DOCUMENTS

| | | | | |
|---|---|---|---|---|
| EP | 1920824 | * | 5/2008 | ................ C07F 9/28 |
| EP | 1920824 A | | 5/2008 | |

OTHER PUBLICATIONS

Ohno, et al, "Chapter 1: Importance and Possibilty of Ionic Liquids," (2005), pp. 1-4.*
Kazarian et al "High-pressure $CO_2$ induced reduction of the melting temperature of ionics liquids", Chem. Commun., 2002 1314-1315.
Jianbin Tang et al, "Poly(ionic liquid)s: a new material with enhanced and fast $CO_2$ absorption", Chem. Commun. 2005, 3325-3327.
Welton, Thomas, "Room-Temperature Ionic Liquids, Solvents for Synthesis and Catalysis", Chem. Rev. 1999 99, 2071-2083.
Seddon et al, "Ionic Liquids for Clean Technology", J. Chem. Tech. Biotechnol., 1997, 68, 351-356.
Gordon et al, "Ionic Liquid Crystals: Hexafluorophosphate Salts", J. Mater. Chem. 1998, 8, 2627-2636.
Holl et al, "Cell Nucleation in Solid-State Polymeric Foams: Evidence of a Triaxial Tensile Failure Mechanism", Journal of Materials Science, 34 (1999) 637-644.
Enderby, John. E., "Ionic Liquids: Recent Progress and Remaining Problems", J. Phys. Condens. Matter, 5 (1993) B99-B106.
Amajjahe et al, "Microwave-Sensitive Foamable Poly(ionic liquids) Bearing tert-Butyl Ester Groups: Influence of Counterions on the Eseter Pyrolysis", Macromolecular Rapid Communications, 2009, 30, 94-98.
Miller et al, "Microcellular and Nanocellular Solid-State Polyetherimide (PEI) Foams Using Sub-Critical Carbon Dioxide I. Processing and Structure", Polymer, 50, (2009) 5576-5584.

* cited by examiner

Primary Examiner — Kamal Saeed
Assistant Examiner — Janet L Coppins

(57) ABSTRACT

Foams of ionic compounds are described. Methods of making the foams are also provided. The foams are ionic and can be used for catalysis, separations, gas storage, biosensors, electronics, and electrochemical applications.

19 Claims, No Drawings

FOAMED IONIC COMPOUNDS

This application claims priority under 35 U.S.C. §119(e) from, and claims the benefit of, U.S. Provisional Application No. 61/288,506, filed Dec. 21, 2009, and U.S. Provisional Application No. 61/288,10, filed Dec. 21, 2009, each of which is by this reference incorporated in its entirety as a part hereof for all purposes.

TECHNICAL FIELD

The invention relates to the field of foams. More specifically, the invention relates to foams of an ionic compound and methods of making the foams.

BACKGROUND

Foams are typically made of organic polymers, such as polyurethane, and are widely used as thermal insulating building materials, adhesives, cellular scaffolding for bone regeneration, and for acoustical vibration control. Conductive polyurethane foams are also known.

Conductive polyurethane foams are prepared in various ways. For example, metal ion salts or conductive solid fillers, such as carbon or metals, can be added to the foam formulation, or conductive polyurethane foams can be made by imbibing the foam with a solvent containing a conductive material. A polyurethane foam can also be coated with a conductive material to form a conductive foam. More recently, U.S. Patent Application Publication No. 2008/0073622 has described conductive polyurethane foams that are produced using a foam formulation and a conductive component that has at least one organic compound, such as an ionic liquid, at least one metal salt and/or combinations thereof.

Foamable poly(ionic liquids) bearing tert-butyl ester groups that are microwave sensitive have been prepared by Amajjahe et al as described in *Macromol. Rapid Commun.* 30:94-98, 2009.

Although polyurethane provide a foam with useful properties, a need remains for ionic foams, which would be useful for many additional applications such as catalysis, separations, gas storage, biosensors, electronic and electrochemical applications.

SUMMARY

The inventions hereof address the above need by providing, in one embodiment, a foam that is prepared from an ionic compound, and methods of preparing the foam.

Accordingly, in one embodiment, the inventions hereof provide a foam that includes, and/or can be prepared from, an ionic compound and/or a compound that is a solid at a temperature above about 20° C. In another alternative embodiment hereof, a foam hereof consists essentially of an ionic compound.

In another alternative embodiment hereof, a foam hereof is non-polymeric, includes a non-polymeric composition and/or is formed from a non-polymeric composition. In another alternative embodiment hereof, a foam hereof is an ionic foam. In another alternative embodiment hereof, a foam hereof is electrically conductive. In another alternative embodiment hereof, a foam hereof is flexible or rigid. In another alternative embodiment hereof, a foam hereof is a solid state foam. In another alternative embodiment hereof, a foam hereof is open-cell or closed cell. In another alternative embodiment hereof, a foam hereof is microcellular or nanocellular.

In a further embodiment hereof, the inventions hereof provide an ionic, non-polymeric foam.

In yet another embodiment hereof, the inventions hereof provide a foam that consists essentially of at least one ionic, non-polymeric composition or ionic compound.

In yet another embodiment hereof, the inventions hereof provide a method of making a foam comprising (a) exposing a solid, ionic non-polymeric composition or an ionic compound to a blowing agent under pressure for a time sufficient to liquefy the composition or compound, thereby forming a metastable liquid comprising the composition or compound and the blowing agent; and (b) reducing the pressure to release the blowing agent from the metastable liquid, thereby forming an ionic foam.

In yet another embodiment hereof, the inventions hereof provide a method of making a foam comprising (a) heating an ionic non-polymeric composition or an ionic compound to a temperature sufficient to form a liquid therefrom; (b) adding a blowing agent to the composition or compound, thereby forming a composition comprising the ionic compound and the blowing agent; (c) cooling the composition to a temperature sufficient to form therefrom a metastable liquid comprising the ionic compound and the blowing agent; and (d) removing the blowing agent from the metastable liquid, thereby forming an ionic foam.

Also provided are methods of making an ionic foam, and various uses of the foam.

DETAILED DESCRIPTION

As used above and throughout the description of the invention, the following terms, unless otherwise indicated, shall be defined as follows:

The terms "foam", "foamed ionic compound" and/or "ionic foam" refer to a solid material that is formed by trapping gas bubbles in an ionic compound. An ionic foam is characterized by the presence therein of the same charged species that are contained in the ionic compound.

The term "blowing agent" refers to a gaseous composition that is used to enhance the expansion of a foam.

The term "metastable liquid" refers to a liquid composition comprising a dissolved gas, wherein the dissolved gas is present at a concentration above its solubility limit.

Disclosed herein is a foam that includes and/or is prepared from an ionic compound. Also disclosed herein is an ionic foam, which can further be a non-polymeric foam. The foams disclosed herein can be used for catalysis, separations, gas storage, biosensors, electronic, and electrochemical applications.

Ionic Compounds

Ionic compounds are formed from and contain therein charged species such as ions. Ionic compounds suitable for use herein to prepare a foam preferably include ionic compounds that exist as solids at a temperature above about 20° C. Many such ionic compounds are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic compound. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups. Various triarylphosphines, thioethers and cyclic and non-cyclic quaternary ammonium salts may also be used for this purpose. Ionic compounds suitable for use herein may also be synthesized by salt metathesis, by an acid-base neutralization reaction or by quaternizing a selected nitrogen-containing compound; or they may be obtained commercially from several companies such as Merck (Darmstadt, Germany), BASF (Mount Olive, N.J.), Fluka Chemical Corp. (Milwaukee, Wis.), and Sigma-Aldrich (St. Louis, Mo.).

Representative examples of ionic compounds suitable for use herein are included among those that are described in sources such as *J. Chem. Tech. Biotechnol.*, 68:351-356 (1997); *Chem. Ind.*, 68:249-263 (1996); *J. Phys. Condensed Matter*, 5: (supp 34B):B99-B106 (1993); *Chemical and Engineering News, Mar.* 30, 1998, 32-37; *J. Mater. Chem.*, 8:2627-2636 (1998); *Chem. Rev.*, 99:2071-2084 (1999); and US 2004/0133058 and US 2008/0028777 (each of which is by this reference incorporated in its entirety as a part hereof for all purposes). In one embodiment, a library, i.e. a combinatorial library, of ionic compounds may be prepared, for example, by preparing various alkyl derivatives of a quaternary ammonium cation, and varying the associated anions. The acidity of the ionic compounds can be adjusted by varying the molar equivalents and type and combinations of Lewis acids.

Ionic compounds suitable for use herein include an anion and a cation, and the cation, in various alternative embodiments, may be selected from the group consisting of cations represented by the structures of the following formulae:

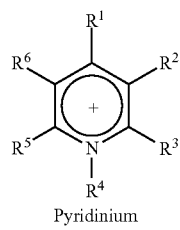
Pyridinium

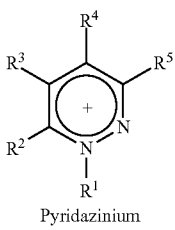
Pyridazinium

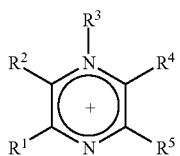
Pyrimidinium

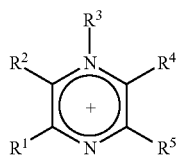
Pyrazinium

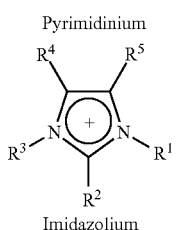
Imidazolium

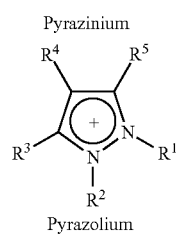
Pyrazolium

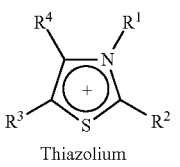
Thiazolium

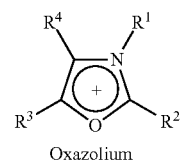
Oxazolium

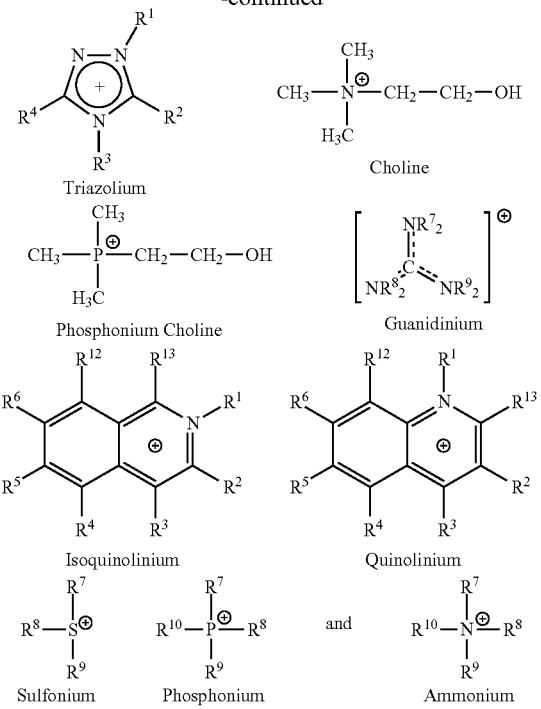

wherein:
(a) $R^1$, $R^2$, $R^3$, $R^4$, $R^5$, $R^6$, $R^{12}$ and $R^{13}$ are independently selected from the group consisting of:
  (i) H,
  (ii) halogen,
  (iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
  (iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
  (v) $C_6$ to $C_{20}$ unsubstituted aryl, or $C_3$ to $C_{25}$ unsubstituted heteroaryl having one to three heteroatoms independently selected from the group consisting of O, N, Si and S;
  (vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
    (A) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
    (B) OH,
    (C) $NH_2$, and
    (D) SH; and
  (vii) —$(CH_2)_n$, $Si(CH_2)_mCH_3$, —$(CH_2)_nSi(CH_3)_3$, —$(CH_2)_nOSi(CH_3)_m$, where n is independently 1-4 and m is independently 0-4;
b) $R^7$, $R^8$, $R^9$, and $R^{10}$ are independently selected from the group consisting of:

(i) —CH₃, —C₂H₅, or C₃ to C₂₅ straight-chain, branched or cyclic alkane or alkene, optionally substituted with at least one member selected from the group consisting of Cl, Br, F, I, OH, NH₂ and SH;

(ii) —CH₃, —C₂H₅, or C₃ to C₂₅ straight-chain, branched or cyclic alkane or alkene comprising one to three heteroatoms selected from the group consisting of O, N, Si and S, and optionally substituted with at least one member selected from the group consisting of Cl, Br, F, I, OH, NH₂ and SH;

(iii) C₆ to C₂₅ unsubstituted aryl, or C₃ to C₂₅ unsubstituted heteroaryl having one to three heteroatoms independently selected from the group consisting of O, N, Si and S; and (iv) C₆ to C₂₅ substituted aryl, or C₃ to C₂₅ substituted heteroaryl having one to three heteroatoms independently selected from the group consisting of O, N, Si and S; and wherein said substituted aryl or substituted heteroaryl has one to three substituents independently selected from the group consisting of:

(A) —CH₃, —C₂H₅, or C₃ to C₂₅ straight-chain, branched or cyclic alkane or alkene, optionally substituted with at least one member selected from the group consisting of Cl, Br, F, I, OH, NH₂ and SH, (B) OH,
(C) NH₂, and
(D) SH; and (v) —(CH₂)ₙSi(CH₂)ₘCH₃, —(CH₂)ₙSi (CH₃)₃, —(CH₂)ₙOSi(CH₃)ₘ, where n is independently 1-4 and m is independently 0-4; and c) optionally, at least two of R¹, R², R³, R⁴, R⁵, R⁶, R⁷, R⁸, R⁹, and R¹⁰ can together form a cyclic or bicyclic alkanyl or alkenyl group.

In other alternative embodiments, an ionic compound includes a cation selected from one or more members of the group consisting of pyridinium, pyridazinium, pyrimidinium, pyrazinium, imidazolium, pyrazolium, thiazolium, oxazolium, triazolium, phosphonium, ammonium, benzyltrimethylammonium, choline, dimethylimidazolium, guanidinium, phosphonium choline, tetramethylammonium, and tetraethylphosphonium.

In another embodiment, ionic compounds suitable for use herein include those having fluorinated cations wherein at least one member selected from R¹, R², R³, R⁴, R⁵, R⁶, R⁷, R⁸, R⁹ and R¹⁰, as described above, comprises F⁻.

In other alternative embodiments, an ionic compound as used herein includes an anion selected from one or more members of the group consisting of: [CH₃CO₂]⁻, [HSO₄]⁻, [CH₃OSO₃]⁻, [C₂H₅OSO₃]⁻, [AlCl₄]⁻, [CO₃]²⁻, [HCO₃]⁻, [NO₂]⁻, [NO₃]⁻, [SO₄]²⁻, [PO₃]³⁻, [HPO₃]²⁻, [H₂PO₃]¹⁻, [PO₄]³⁻, [HPO₄]²⁻, [H₂PO₄]⁻, [HSO₃]⁻, [CuCl₂]⁻, Cl⁻, Br⁻, I⁻, SCN⁻; carborates optionally substituted with alkyl or substituted alkyl; carboranes optionally substituted with alkylamine, substituted alkylamine, alkyl or substituted alkyl; and a fluorinated anion.

In other alternative embodiments, an ionic compound as used herein includes an anion selected from one or more members of the group consisting of aminoacetate, ascorbate, benzoate, catecholate, citrate, dimethylphosphate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, [CH₃CO₂]⁻, [HSO₄]⁻, [CH₃OSO₃]⁻, [C₂H₅OSO₃]⁻, [AlCl₄]⁻, [CO₃]²⁻, [HCO₃]⁻, [NO₂]⁻, [NO₃]⁻, [SO₄]²⁻, [PO₄]³⁻, [HPO₄]²⁻, [H₂PO₄]⁻, [HSO₃]⁻, [CuCl₂]⁻, Cl⁻, Br⁻, I⁻, SCN⁻, [BF₄]⁻, [PF₆]⁻, [SbF₆]⁻, [CF₃SO₃]⁻, [HCF₂CF₂SO₃]⁻, [CF₃HFCCF₂SO₃]⁻, [HCClFCF₂SO₃]⁻, [(CF₃SO₂)₂N]⁻, [(CF₃CF₂SO₂)₂N]⁻, [(CF₃SO₂)₃C]⁻, [CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂ICF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻, F⁻, and anions represented by the structure of the following formula:

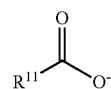

wherein R¹¹ is selected from the group consisting of:

(a) —CH₃, —C₂H₅, or C₃ to C₁₀ straight-chain, branched or cyclic alkane or alkene, optionally substituted with at least one member selected from the group consisting of Cl, Br, F, I, OH, NH₂ and SH;

(b) —CH₃, —C₂H₅, or C₃ to C₁₀ straight-chain, branched or cyclic alkane or alkene comprising one to three heteroatoms selected from the group consisting of O, N, Si and S, and optionally substituted with at least one member selected from the group consisting of Cl, Br, F, I, OH, NH₂ and SH;

(c) C₆ to C₁₀ unsubstituted aryl, or C₃ to C₁₀ unsubstituted heteroaryl having one to three heteroatoms independently selected from the group consisting of O, N, Si and S; and (d) C₆ to C₁₀ substituted aryl, or C₃ to C₁₀ substituted heteroaryl having one to three heteroatoms independently selected from the group consisting of O, N, Si and S; and wherein said substituted aryl or substituted heteroaryl has one to three substituents independently selected from the group consisting of:

(i) —CH₃, —C₂H₅, or C₃ to C₁₀ straight-chain, branched or cyclic alkane or alkene, optionally substituted with at least one member selected from the group consisting of Cl, Br, F, I, OH, NH₂ and SH, (ii) OH,
(iii) NH₂, and
(iv) SH.

In yet another embodiment, ionic compounds suitable for use herein comprise a cation selected from the group consisting of pyridinium, pyridazinium, pyrimidinium, pyrazinium, imidazolium, pyrazolium, thiazolium, oxazolium, triazolium, phosphonium, and ammonium ions, as described above; and an anion selected from the group consisting of [CH₃CO₂]⁻, [HSO₄]⁻, [CH₃OSO₃]⁻, [C₂H₅OSO₃]⁻, [AlCl₄]⁻, [CO₃]²⁻, [HCO₃]⁻, [NO₂]⁻, [NO₃]⁻, [SO₄]²⁻, [PO₄]³⁻, [HPO₄]²⁻, [H₂PO₄]⁻, [HSO₃]⁻, [CuCl₂]⁻, Cl⁻, Br⁻, I⁻, SCN⁻; and any fluorinated anion. In yet another embodiment, ionic compounds suitable for use herein comprise a cation selected from the group consisting of pyridinium, pyridazinium, pyrimidinium, pyrazinium, imidazolium, pyrazolium, thiazolium, oxazolium, triazolium, phosphonium, and ammonium ions, as described above; and an anion selected from the group consisting of [BF₄]⁻, [PF₆]⁻, [SbF₆]⁻, [CF₃SO₃]⁻, [HCF₂CF₂SO₃]⁻, [CF₃HFCCF₂SO₃]⁻, [HCClFCF₂SO₃]⁻, [(CF₃SO₂)₂N]⁻, [(CF₃CF₂SO₂)₂N]⁻, [(CF₃SO₂)₃C]⁻, [CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂₁CF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻, and F⁻.

In still another embodiment, ionic compounds suitable for use herein have a cation selected from the group consisting of pyridinium, pyridazinium, pyrimidinium, pyrazinium, imidazolium, pyrazolium, thiazolium, oxazolium, triazolium, phosphonium, and ammonium ions, as described above, wherein at least one member selected from $R^1$, $R^2$, $R^3$, $R^4$, $R^5$, $R^6$, $R^7$, $R^8$, $R^9$, and $R^{10}$ comprises $F^-$; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and any fluorinated anion. In still another embodiment, ionic compounds suitable for use herein have a cation selected from the group consisting of pyridinium, pyridazinium, pyrimidinium, pyrazinium, imidazolium, pyrazolium, thiazolium, oxazolium, triazolium, phosphonium, and ammonium ions, as described above, wherein at least one member selected from $R^1$, $R^2$, $R^3$, $R^4$, $R^5$, $R^6$, $R^7$, $R^8$, $R^9$, and $R^{10}$ comprises $F^-$; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In still another embodiment, ionic compounds suitable for use in this invention include those comprising:

a) imidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, $[CH_3OSO_3]^-$;

b) 1-butyl-3-methylimidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

c) 1-propyl-2,3-dimethylimidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

d) 1-ethyl-3-methylimidazolium as the cation, and $[(CF_3CF_2SO_2)_2N]^-$, $[PF_6]^-$, and $[HCF_2CF_2SO_3]^-$ as the anion;

e) 1-propyl-3-methylpyridinium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_{21}CF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

f) 1,2-dimethyl-3-propylimidazolium as the cation, and an anion selected from the group consisting of $[(CF_3SO_2)_3C]^-$ and $[(CF_3SO_2)_2N]^-$;

g) 3-methyl-1-propylpyridinium as the cation, and $[(CF_3SO_2)_2N]^-$ as the anion;

h) 1-butyl-3-methylpyridinium as the cation, and $[(CF_3SO_2)_2N]^-$ as the anion;

i) 1-dodecyl-3-methylimidazolium as the cation, and $[HCF_2CF_2SO_3]^-$ as the anion;

j) 1-heptyl-3-methylimidazolium as the cation, and $[HCF_2CF_2SO_3]^-$ as the anion;

k) tetradecyl(trihexyl)phosphonium as the cation, and $[CF_3CF_2OCFHCF_2SO_3]^-$ or $[CF_3OCFHCF_2SO_3]^-$ as the anion;

l) tributyl(tetradecyl)phosphonium as the cation, and $[CF_3HFCCF_2SO_3]^-$ as the anion;

m) 1,3-dioctylimidazolium or 1-octyl-3-methylimidazolium as the cation, and $[I]^-$ as the anion.

Other cations suitable as part of an ionic compound as used herein include 1,2-dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butylpyridinium, 1-butyl-4-methylpyridinium, 1,3-dimethylimidazolium, 1,2,3-trimethylimidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazol, 3-butyl-1-methylimidazolium, 3-butyl-1-ethylimidazolium, 3-butyl-1,2-dimethylimidazolium, 1,3-di-n-Butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium and 1-decyl-3-methylimidazolium ions.

In yet another embodiment, ionic compounds suitable for use herein also include those selected from the group consisting of:

a) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above;

b) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine;

c) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above; and having an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion;

d) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above;

and having an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$;

e) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine; and having an anion selected from the group consisting of $[CH_3CO_2]^-$, $[HSO_4]^-$, $[CH_3OSO_3]^-$, $[C_2H_2OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion; and f) an ionic compound having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine; and having an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In yet another embodiment, ionic compounds suitable for use herein also include those selected from the group consisting of:

g) an ionic compound having an imidazolium cation or a fluorinated imidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

h) an ionic compound having a 1-ethyl-3-methylimidazolium or a fluorinated 1-ethyl-3-methylimidazolium as the cation, and $[(CF_3CF_2SO_2)_2N]^-$ as the anion;

i) an ionic compound having a 1-butyl-3-methylimidazolium cation or a fluorinated 1-butyl-3-methylimidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2C)CF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

j) an ionic compound having a 1-propyl-2,3-dimethylimidazolium cation or a fluorinated 1-propyl-2,3-dimethylimidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2C)CF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

k) an ionic compound having a 1-propyl-3-methylimidazolium cation or a fluorinated 1-propyl-3-methylimidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

l) an ionic compound having a 1,2-dimethyl-3-propylimidazolium cation or a fluorinated 1,2-dimethyl-3-propylimidazolium cation; and an anion selected from the group consisting of $[(CF_3SO_2)_3C]^-$ and $[(CF_3SO_2)_2N]^-$;

m) an ionic compound having a 3-methyl-1-propylpyridinium cation or a fluorinated 3-methyl-1-propylpyridinium cation, and $[(CF_3SO_2)_2N]^-$ as the anion;

n) an ionic compound having a 1-butyl-3-methylpyridinium cation or a fluorinated 1-butyl-3-methylpyridinium cation, and $[(CF_3SO_2)_2N]^-$ as the anion;

o) an ionic compound having a 1-dodecyl-3-methylimidazolium cation or a fluorinated 1-dodecyl-3-methylimidazolium cation, and $[HCF_2CF_2SO_3]^-$ as the anion;

p) an ionic compound having a 1-heptyl-3-methylimidazolium cation or a fluorinated 1-heptyl-3-methylimidazolium cation, and $[HCF_2CF_2SO_3]^-$ as the anion;

q) an ionic compound having a tetradecyl(trihexyl)phosphonium cation or a fluorinated tetradecyl(trihexyl)phosphonium cation, and $[CF_3CF_2OCFHCF_2SO_3]^-$ or $[CF_3OCFHCF_2SO_3]^-$ as the anion;

r) an ionic compound having a tributyl(tetradecyl)phosphonium cation or a fluorinated tributyl(tetradecyl)phosphonium cation, and $[CF_3HFCCF_2SO_3]^-$ as the anion; and s) an ionic compound having a cation selected from the group consisting of 1,3-dioctylimidazolium, 1-octyl-3-methylimidazolium, fluorinated 1,3-dioctylimidazolium, or fluorinated 1-octyl-3-methylimidazolium ions, and $[I]^-$ as the anion.

In another alternative embodiment, an ionic compound as used herein is 1-butyl-3-methylimidazolium chloride.

Accordingly, in one embodiment, the inventions hereof provide an ionic foam, or a foam that includes, and/or can be prepared from an ionic compound (such as a non-polymeric ionic compound), which compound is preferably a solid at a temperature above about 20° C. In another alternative embodiment hereof, a foam hereof consists essentially of an ionic compound.

In another alternative embodiment hereof, a foam hereof is non-polymeric, includes a non-polymeric composition or compound, and/or is formed from a non-polymeric composition or compound. A non-polymeric foam is a foam that does not contain, excludes and has not been prepared to any extent from an oligomer, a polymer (such as a polyurethane or polystyrene) or a polymeric composition. An ionic, non-polymeric composition is a composition that contains an ionic compound and other components, but does not contain, excludes and is not prepared to any extent from a polymer (such as a polyurethane or polystyrene) or an oligomer, and in which neither the composition nor the ionic compound have to any extent been polymerized. A non-polymeric compound is a compound that does not contain, excludes and is not prepared to any extent from a polymer (such as a polyurethane or polystyrene) or an oligomer, and that has not to any extent been polymerized. Where a foam hereof consists essentially of a non-polymeric composition or an ionic compound, it does not contain, excludes and is not prepared to any extent from a polymer (such as a polyurethane or polystyrene) or an oligomer, and in which neither the composition nor the ionic compound have to any extent been polymerized.

An ionic compound suitable for use herein preferably is a solid up to at least about 25° C., or is a solid up to at least about 30° C., or is a solid up to at least about 35° C., or is a solid up to at least about 40° C., or is a solid up to at least about 45° C., or is a solid up to at least about 50° C., or is a solid up to at least about 55° C. An ionic compound suitable for use herein preferably has in addition, however, a melting temperature that is about 150° C. or less, or a melting temperature that is about 125° C. or less, or a melting temperature that is about 110° C. or less, or a melting temperature that is about 100° C. or less, or a melting temperature that is about 95° C. or less, or a melting temperature that is about 90° C. or less.

In another alternative embodiment hereof, a foam hereof is an ionic foam. In another alternative embodiment hereof, a foam hereof is electrically conductive. In another alternative embodiment hereof, a foam hereof is flexible or rigid. In another alternative embodiment hereof, a foam hereof is a solid state foam. In another alternative embodiment hereof, a foam hereof is open-cell or closed cell. In another alternative embodiment hereof, a foam hereof is microcellular or nanocellular.

Methods of Making Ionic Solid-State Foam

In one embodiment, a foam as provided herein is prepared from at least one non-polymeric composition or ionic compound that is in a solid state. The solid composition or compound is exposed under pressure to a blowing agent for a time sufficient to liquefy the composition or compound, thereby forming a metastable liquid comprising the liquefied composition or compound, and the blowing agent. The composition or compound absorbs the blowing agent, which lowers its melting temperature, resulting in the formation of the metastable liquid. The non-polymeric composition or ionic compound may be exposed to the blowing agent at an elevated pressure to accelerate its liquefaction. The composition or compound can be exposed to the blowing agent at a pressure that is at least about 1 atm, or is at least about 1.25 atm, or is at least about 1.5 atm, or is at least about 2 atm, or is at least about 3 atm, or is at least about 5 atm, and yet is about 10 atm or less, or is about 7.5 atm or less, or is about 5 atm or less, or is about 3 atm or less, or is about 2 atm or less, or is about 1.5 atm or less.

Blowing agents suitable for use herein to prepare a foam include blowing agents that are in the gaseous state at atmospheric pressure and room temperature, many of which are known in the art. Examples of useful blowing agents include without limitation carbon dioxide, ammonia, fluorocarbons such as tetrafluoromethane (Freon 14), fluoroform (Freon 23), and hexafluoroethane (Freon 116); hydrofluorocarbons such as difluoromethane (HFC-32), 1,1-difluoroethane, 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a), fluoroethane (HFC-161), pentafluoroethane (HFC-125), 1,1,1,3,3-pentafluoropropane (HFC-245fa), and 1,1,1,3,3-pentafluorobutane (HFC-365mfc); fluoro-olefins such as 2,3,3,3-tetrafluoroprop-1-ene (HFO-1234yf); and mixtures thereof.

In another alternative embodiment, the blowing agent is selected from the group consisting of ammonia, difluoromethane, 1,1,1,2-tetrafluoroethane, carbon dioxide, and 2,3,3,3-tetrafluoroprop-1-ene. In another alternative embodiment, the ionic compound absorbs at least about 25 mole percent of the blowing agent relative to the moles of the ionic compound.

Various additives may be incorporated into the foamed ionic compound by adding them to the metastable liquid. Suitable additives include, but are not limited to, surfactants, colorants, flame retardants, antimicrobials, plasticizers, antioxidants, and the like.

The pressure is reduced to release the blowing agent from the metastable liquid, thereby forming a foam from the non-polymeric composition or the ionic compound. The blowing agent may be released from the metastable liquid in a variety of ways including, for example, by vigorously agitating the liquid. Alternatively, the blowing agent may be released from the metastable liquid by ejecting the metastable liquid from an elevated pressure to atmospheric pressure. The rate of release of the blowing agent can be used to control the porosity of the foam thereby formed.

In another alternative embodiment, a foam may be prepared from at least one non-polymeric composition ionic compound that is in a liquid state. In this embodiment, the composition or compound is heated to a temperature sufficient to melt the composition or compound, thereby forming a liquid therefrom. A blowing agent is then added to the liquid, thereby forming a liquid composition that includes the non-polymeric composition or ionic compound and the blowing agent. The blowing agent may be added by bubbling it through the liquid composition or compound for a time sufficient to saturate the composition or compound with the blowing agent. The blowing agent may be added at atmospheric pressure or at an elevated pressure, as set forth above.

In another alternative embodiment, the composition or compound absorbs at least about 25 mole percent of the blowing agent relative to the moles of composition or compound. In another alternative embodiment, the composition or compound expands in volume by at least about 10% relative to its initial volume upon absorption of the blowing agent.

The liquid composition is then cooled to a temperature below the melting temperature of the ionic compound, or to room temperature, e.g. about 20~25° C., thereby forming a metastable liquid that contains the non-polymeric composition or ionic compound and the blowing agent. Then, the blowing agent is removed from the metastable liquid, thereby forming a foam from the composition or compound. The blowing agent may be removed or driven from the metastable liquid in the same manner as described above, such as by reduction or pressure or agitation.

Other methods of preparing a foam are set forth in Journal of Materials Science 34 (1999) 637~644, and Polymer 50 (2009) 5576-5584.

Various additives, as described above, may be incorporated into the foam by adding them to the non-polymeric composition or ionic compound, the liquid composition of the composition or compound, and/or the metastable liquid.

Uses of a Ionic Foam

The foamed non-polymeric compositions or ionic compounds hereof, the foams prepared from non-polymeric compositions or ionic compounds as herein, and the ionic foams prepared by the methods hereof, have many potential applications. For example, these foams are useful as catalysts for chemical transformations. In this embodiment, a suitable catalyst may be introduced into the metastable liquid or the composition or compound before the formation of the foam.

The foams may also be used for gas storage applications due to their ability to absorb quantities of gases such as carbon dioxide. For such applications, the foam may be incorporated into a gas storage device.

Due to the electrical conductivity of the compositions or compounds from which they are prepared, the foams hereof are conductive and may be used in the manufacture of biosensors and electrodes for sensing applications. In this embodiment, a foam hereof is incorporated into the biosensor or electrode.

Additionally, the foams hereof are useful in electrochemical cells, including fuel cells and batteries. In this embodiment, a foam hereof is used as an electrode, electrode component, and/or electrochemical cell separator.

The foams hereof may also be used as immobilization supports for the immobilization of biological materials, for example, enzymes, antibodies, nucleic acids, and microbial cells. In this embodiment, the biological material may be adsorbed onto or chemically attached to the foam. The immobilization support may be used, for example, for biocatalysis.

The foams hereof may also be used as a separation membrane to separate ionic from non-ionic materials.

Additionally, the foams hereof may be used in electronic applications, for example, as an anti-static material for protecting sensitive electronics during shipping, handling and/or storage.

EXAMPLES

This invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Example 1

Preparation of Ionic Solid-State Foam Using Ammonia as Blowing Agent

Approximately 10.3 g of 1-butyl-3-methylimidazolium chloride [bmim][Cl], obtained from Aldrich (Milwaukee Wis.), was melted at 85° C. in a round bottom flask using a standard laboratory heating mantle with stirring bar to form an ionic liquid. Ammonia gas was bubbled through the liquid overnight using a glass dip tube submerged beneath the surface of the liquid. The ionic liquid swelled in the presence of the dissolved gas by about 20 to 30%. The liquid was slowly cooled and a metastable liquid formed at ambient temperature (i.e. 23° C.) and pressure. The dissolved ammonia was released from the metastable liquid by increasing the rate of mixing, which led to foaming and solidification of the ionic liquid, producing an ionic solid-state foam.

Example 2

Preparation of Ionic Solid-State Foam Using Difluoromethane as Blowing Agent

Approximately 12.1 g of [bmim][Cl] was melted at 85° C. in a round bottom flask using a standard laboratory heating mantle with stirring bar to form an ionic liquid. Difluoromethane gas, obtained from DuPont Fluoroproducts (Wilmington Del.), was bubbled through the liquid overnight using a glass dip tube submerged beneath the surface of the liquid. The ionic liquid swelled in the presence of the dissolved gas by about 25 to 35%. The liquid was slowly cooled and a metastable liquid formed at ambient temperature (i.e. 23° C.) and pressure. The dissolved difluoromethane was released from the metastable liquid by increasing the rate of mixing, which led to foaming and solidification of the ionic liquid, producing an ionic solid-state foam.

Example 3

Preparation of Ionic Solid-State Foam Using 1,1,1,2-Tetrafluoroethane as Blowing Agent Approximately 11.3 g of [bmim][Cl] was melted at 85° C. in a round bottom flask using a standard laboratory heating mantle with stirring bar to form an ionic liquid. 1,1,1,2-Tetrafluoroethane gas, obtained from DuPont Fluoroproducts (Wilmington Del.), was bubbled through the liquid overnight using a glass dip tube submerged beneath the surface of the liquid. The ionic liquid swelled in the presence of the dissolved gas by about 20 to 35%. The liquid was slowly cooled and a metastable liquid formed at ambient temperature (i.e. 23° C.) and pressure. The dissolved 1,1,1,2-tetrafluoroethane was released from the metastable liquid by increasing the rate of mixing, which led to foaming and solidification of the ionic liquid, producing an ionic solid-state foam.

Example 4

Preparation of Ionic Solid-State Foam Using Carbon Dioxide as Blowing Agent

Approximately 10.8 g of [bmim][Cl] was melted at 85° C. in a round bottom flask using a standard laboratory heating mantle with stirring bar to form an ionic liquid. Carbon dioxide gas was bubbled through the liquid overnight using a glass dip tube submerged beneath the surface of the liquid. The ionic liquid swelled in the presence of the dissolved gas by about 20 to 35%. The liquid was slowly cooled and a metastable liquid formed at ambient temperature (i.e. 23° C.) and pressure. The dissolved carbon dioxide was released from the metastable liquid by increasing the rate of mixing, which led to foaming and solidification of the ionic liquid, producing an ionic solid-state foam.

Example 5

Preparation of Ionic Solid-State Foam Using 2,3,3,3-Tetrafluoroprop-1-ene as Blowing Agent Approximately 10.0 g of [bmim][Cl] was melted at 85° C. in a round bottom flask using a standard laboratory heating mantle with stirring bar to form an ionic liquid. 2,3,3,3-Tetrafluoroprop-1-ene gas, obtained from DuPont Fluoroproducts (Wilmington Del.), was bubbled through the liquid overnight using a glass dip tube submerged beneath the surface of the liquid. The ionic liquid swelled in the presence of the dissolved gas by about 10 to 20%. The liquid was slowly cooled and a metastable liquid formed at ambient temperature (i.e. 23° C.) and pressure. The dissolved 2,3,3,3-tetrafluoroprop-1-ene was released from the metastable liquid by increasing the rate of mixing, which led to foaming and solidification of the ionic liquid, producing an ionic solid-state foam.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. An ionic, non-polymeric foam that comprises an ionic compound wherein the ionic compound comprises an anion selected from the group consisting of
   (a) aminoacetate, ascorbate, benzoate, catecholate, citrate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, and tropolonate;
   (b) $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[HSO_3]^-$, $[CuCl_2]^-$, $Cl^-$, $Br^-$, $I^-$, $SCN^-$; carborates optionally substituted with alkyl or substituted alkyl groups; and carboranes optionally substituted with alkylamine, substituted alkylamine, alkyl or substituted alkyl groups;
   (c) $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]$, $[CF_2ICF_2OCF_2CF_2SO_3]$, $[CF_3CF_2OCF_2CF_2SO_3]^-$, $[(CF_2HCF_2SO_2)_2N]_-$, $[(CF_3CFHCF_2SO_2)_2N]^-$, and $F^-$; and
   (d) anions represented by the structure of the following formula:

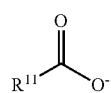

wherein $R^{11}$ is selected from the group consisting of:
   (i) $-CH_3$, $-C_2H_5$, or a $C_3$ to $C_{10}$ straight-chain, branched or cyclic alkane or alkene group, optionally substituted with at least one member selected from the group consisting of Cl, Br, F, I, OH, $NH_2$ and SH;

(ii) $-CH_3$, $-C_2H_5$, or a $C_3$ to $C_{10}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
   (iii) a $C_6$ to $C_{10}$ unsubstituted aryl, or $C_6$ to $C_{10}$ unsubstituted heteroaryl, group having one to three heteroatoms independently selected from the group consisting of O, N, Si and S; and
   (iv) a $C_6$ to $C_{10}$ substituted aryl, or $C_6$ to $C_{10}$ substituted heteroaryl, group having one to three heteroatoms independently selected from the group consisting of O, N, Si and S; and wherein said substituted aryl or substituted heteroaryl group has one to three substituents independently selected from the group consisting of:
      (A) $-CH_3$, $-C_2H_5$, or a $C_3$ to $C_{10}$ straight-chain, branched or cyclic alkane or alkene group, optionally substituted with at least one member selected from the group consisting of Cl, Br, F, I, OH, $NH_2$ and SH,
      (B) OH,
      (C) $NH_2$, and
      (D) SH.

2. A foam according to claim 1 wherein the ionic compound further comprises a cation, and the cation is selected from the group consisting of cations represented by the structures of the following formulae:

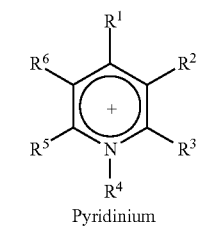 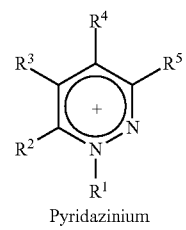

Pyridinium            Pyridazinium

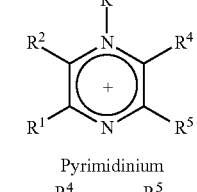 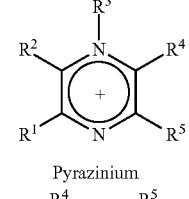

Pyrimidinium          Pyrazinium

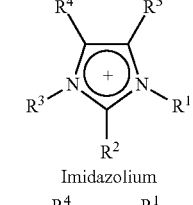 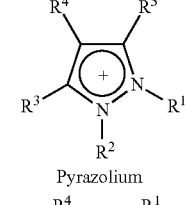

Imidazolium           Pyrazolium

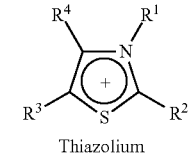 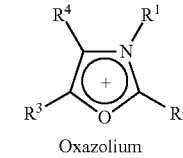

Thiazolium            Oxazolium

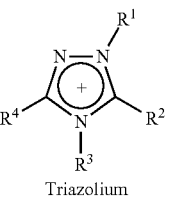 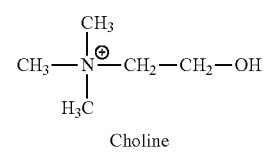

Triazolium            Choline

-continued

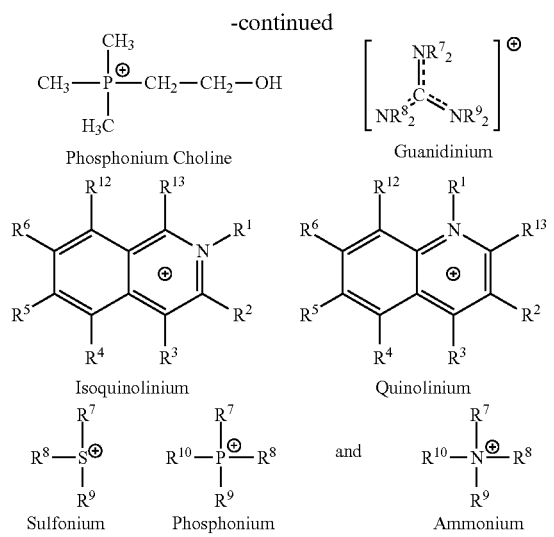

Phosphonium Choline

Guanidinium

Isoquinolinium

Quinolinium

Sulfonium

Phosphonium and

Ammonium wherein:
(a) $R^1$, $R^2$, $R^3$, $R^4$, $R^5$, $R^6$, $R^{12}$ and $R^{13}$ are independently selected from the group consisting of:
(i) H,
(ii) halogen,
(iii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(iv) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected, from the group consisting of Cl, Br, F, I, OH, $NH_2$ and SH;
(v) a $C_6$ to $C_{20}$ unsubstituted aryl, or $C_6$ to $C_{25}$ unsubstituted heteroaryl, group having one to three heteroatoms independently selected from the group consisting of O, N, Si and S;
(vi) a $C_6$ to $C_{25}$ substituted aryl, or $C_6$ to $C_{25}$ substituted heteroaryl, group having one to three heteroatoms independently selected from the group consisting of O, N, Si and S; and wherein said substituted aryl or substituted heteroaryl group has one to three substituents independently selected from the group consisting of:
(A) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH,
(B) OH,
(C) $NH_2$, and
(D) SH; and
(vii) —$(CH_2)_n$, $Si(CH_2)_mCH_3$, —$(CH_2)_nSi(CH_3)_3$, —$(CH_2)_nOSi(CH_3)_m$, where n is independently 1-4 and m is independently 0-4;
(b) $R^7$, $R^8$, $R^9$, and $R^{10}$ are independently selected from the group consisting of:
(i) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(ii) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected, from the group consisting of Cl, Br, F, I, OH, $NH_2$ and SH;
(iii) a $C_6$ to $C_{25}$ unsubstituted aryl, or $C_6$ to $C_{25}$ unsubstituted heteroaryl, group having one to three heteroatoms independently selected from the group consisting of O, N, Si and S; and
(iv) a $C_6$ to $C_{25}$ substituted aryl, or $C_6$ to $C_{25}$ substituted heteroaryl, group having one to three heteroatoms independently selected from the group consisting of O, N, Si and S; and wherein said substituted aryl or substituted heteroaryl group has one to three substituents independently selected from the group consisting of:
(A) —$CH_3$, —$C_2H_5$, or a $C_3$ to $C_{25}$ straight-chain, branched or cyclic alkane or alkene group, optionally substituted with at least one member selected from the group consisting of C, Br, F, I, OH, $NH_2$ and SH,
(B) OH,
(C) $NH_2$, and
(D) SH; and
(v) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4; and
c) optionally, at least two of $R^1$, $R^2$, $R^3$, $R^4$, $R^5$, $R^6$, $R^7$, $R^9$, and $R^{10}$ can together form a cyclic or bicyclic alkanyl or alkenyl group.

3. A foam according to claim 1 wherein the anion is selected from one or more members of the group consisting of: $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[HSO_3]^-$, $[CuCl_2]^-$, $Cl^-$, $Br^-$, $I^-$, $SCN^-$; carborates optionally substituted with alkyl or substituted alkyl groups; and carboranes optionally substituted with alkylamine, substituted alkylamine, alkyl or substituted alkyl groups.

4. An article fabricated from a foam according to claim 1.

5. An article according to claim 4 that comprises a gas storage device, a catalyst, a biosensor or electrode, an immobilization support, a separation membrane, or an electrochemical cell component.

6. A foam according to claim 1 wherein the ionic compound is 1-butyl-3-methylimidazolium chloride.

7. A foam according to claim 1 which is electrically conductive.

8. A foam according to claim 1 which is flexible or rigid.

9. A foam according to claim 1 which is a solid state foam.

10. A foam according to claim 1 which is open-cell or closed cell.

11. A foam according to claim 1 which is microcellular or nanocellular.

12. A foam according to claim 1 wherein the ionic compound further comprises a cation, and wherein the cation and anion are selected from the group consisting of:
a) imidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[CF_3CFHCF_2SO_2)_2N]^-$, and $[CH_3OSO_3]^-$;
b) 1-butyl-3-methylimidazolium as the cation, and an anion selected from the group consisting of $[BF_4]^-$,

[PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

c) 1-propyl-2,3-dimethylimidazolium as the cation, and an anion selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, and [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$], [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻, d) 1-ethyl-3-methylimidazolium as the cation, and an anion selected from the group consisting of [(CF$_3$CF$_2$SO$_2$)$_2$N]⁻, [PF$_6$]⁻, and [HCF$_2$CF$_2$SO$_3$]⁵;

e) 1-propyl-3-methylpyridinium as the cation, and an anion selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

f) 1,2-dimethyl-3-propylimidazolium as the cation, and an anion selected, from the group consisting of [(CF$_3$SO$_2$)$_3$C]⁻ and [(CF$_3$SO$_2$)$_2$N]⁻;

g) 3-methyl-1-propy pyridinium as the cation, and [(CF$_3$SO$_2$)$_2$N]⁻ as the anion;

h) 1-butyl-3-methylpyridinium as the cation, and [(CF$_3$SO$_2$)$_2$N]⁻ as the anion;

i) 1-dodecyl-3-methylimidazolium as the cation, and [HCF$_2$CF$_2$SO$_3$]⁻ as the anion;

j) 1-heptyl-3-methylimidazolium as the cation, and [HCF$_2$CF$_2$SO$_3$]⁻ as the anion;

k) tetradecyl(trihexyl)phosphonium as the cation, and an anion selected from the group consisting of [CF$_3$CF$_2$OCFHCF$_2$SO$_3$]⁻ and [CF$_3$OCFHCF$_2$SO$_3$]⁻;

l) tributyl(tetradecyl)phosphonium as the cation, and [CF$_3$HFCCF$_2$SO$_3$]⁻ as the anion; and m) 1,3-dioctylimidazolium or 1-octyl-3-methylimidazolium as the cation, and [I]⁻ as the anion.

13. A foam according to claim 1 wherein an ionic compound comprises a cation, and the cation is selected from the group consisting of:
1,2-dimethylpyridinium,
1-methyl-2-ethylpyridinium,
1-methyl-2-ethyl-6-methylpyridinium,
N-methylpyridinium,
1-butyl-2-methylpyridinium,
1-butyl-2-ethylpyridinium,
1-butyl-2-ethyl-6-methylpyridinium,
N-butylpyridinium,
1-butyl-4-methylpyridinium,
1,3-dimethylimidazolium,
1,2,3-trimethylimidazolium,
1-n-butyl-3-methylimidazolium,
1,3,4,5-tetramethylimidazolium,
1,3,4-trimethylimidazolium,
2,3-dimethylimidazolium,
1-butyl-2,3-dimethylimidazolium,
3,4-dimethylimidazolium,
2-ethyl-3,4-dimethylimidazolium,
3-methyl-2-ethylimidazol,
3-butyl-1-methylimidazolium,
3-butyl-1-ethylimidazolium,
3-butyl-1,2-dimethylimidazolium,
1,3-di-n-butylimidazolium,
3-butyl-1,4,5-trimethylimidazolium,
3-butyl-1,4-dimethylimidazolium,
3-butyl-2-methylimidazolium,
1,3-dibutyl-2-methylimidazolium,
3-butyl-4-methylimidazolium,
3-butyl-2-ethyl-4-methylimidazolium and
3-butyl-2-ethylimidazolium,
1-meth octylimidazolium and
1-decyl-3-methylimidazolium cations.

14. A foam according to claim 1 wherein the ionic compound further comprises a cation, and wherein the cation and anion are selected from the group consisting of:

d) an imidazolium cation or a fluorinated imidazolium cation; and an anion, selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

e) a 1-ethyl-3-methylimidazolium or a fluorinated 1-ethyl-3-methylimidazolium as the cation, and [(CF$_3$CF$_2$SO$_2$)$_2$N]⁻ as the anion;

f) a 1-butyl-3-methylimidazolium cation or a fluorinated 1-butyl-3-methylimidazolium cation; and an anion selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

g) a 1-propyl-2,3-dimethylimidazolium cation or a fluorinated 1-propyl-2,3-dimethylimidazolium cation; and an anion selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

h) a 1-propyl-3-methylimidazolium cation or a fluorinated 1-propyl-3-methylimidazolium cation; and an anion selected from the group consisting of [BF$_4$]⁻, [PF$_6$]⁻, [SbF$_6$]⁻, [CF$_3$SO$_3$]⁻, [HCF$_2$CF$_2$SO$_3$]⁻, [CF$_3$HFCCF$_2$SO$_3$]⁻, [HCClFCF$_2$SO$_3$]⁻, [(CF$_3$SO$_2$)$_2$N]⁻, [(CF$_3$CF$_2$SO$_2$)$_2$N]⁻, [(CF$_3$SO$_2$)$_3$C]⁻, [CF$_3$CO$_2$]⁻, [CF$_3$OCFHCF$_2$SO$_3$]⁻, [CF$_3$CF$_2$OCFHCF$_2$SO$_3$]⁻, [CF$_3$CFHOCF$_2$CF$_2$SO$_3$]⁻, [CF$_2$HCF$_2$OCF$_2$CF$_2$SO$_3$]⁻, [CF$_2$ICF$_2$OCF$_2$CF$_2$SO$_3$]⁻, [CF$_3$CF$_2$OCF$_2$CF$_2$SO$_3$]⁻, [(CF$_2$HCF$_2$SO$_2$)$_2$N]⁻, and [(CF$_3$CFHCF$_2$SO$_2$)$_2$N]⁻;

i) a 1,2-dimethyl-3-propylimidazolium cation or a fluorinated 1,2-dimethyl-3-propylimidazolium cation; and an anion selected from the group consisting of [(CF$_3$SO$_2$)$_3$C]⁻ and [(CF$_3$SO$_2$)$_2$N]⁻;

j) a 3-methyl-1-propylpyridinium cation or a fluorinated 3-methy-1-propylpyridinium cation, and [(CF$_3$SO$_2$)$_2$N]$^-$ as the anion;

k) a 1-butyl-3-methylpyridinium cation or a fluorinated 1-butyl-3-methylpyridinium cation, and [(CF$_3$SO$_2$)$_2$N]$^-$ as the anion;

l) a 1-dodecyl-3-methylimidazolium cation or a fluorinated 1-dodecyl-3-methylimidazolium cation, and [HCF$_2$CF$_9$SO$_3$]$^-$ as the anion;

m) a 1-heptyl-3-methylimidazolium cation or a fluorinated 1-heptyl-3-methylimidazolium cation, and [HCF$_2$CF$_9$SO$_3$]$^-$ as the anion;

n) a tetradecyl(trihexyl)phosphonium cation or a fluorinated tetradecyl(trihexyl)phosphonium cation, and an anion selected from the group consisting of [CF$_3$CF$_2$OCFHCF$_2$SO$_3$]$^-$ and [CF$_3$OCFHCF$_2$SO$_3$]$^-$;

o) a tributyl(tetradecyl)phosphonium cation, or a fluorinated tributyl(tetradecyl)phosphonium cation, and [CF$_3$HFCCF$_2$SO$_3$]$^-$ as the anion; and p) a cation selected from the group consisting of 1,3-dioctylimidazolium, 1-octyl-3-methylimidazolium, fluorinated 1,3-dioctylimidazolium, and fluorinated 1-octyl-3-methylimidazolium ions, and [I]$^-$ as the anion.

15. A foam according to claim 1 wherein the anion is selected from the (a) group consisting of aminoacetate, ascorbate, benzoate, catecholate, citrate, formate, fumarate, gallate, glycolate, glyoxylate, iminodiacetate, isobutyrate, kojate, lactate, levulinate, oxalate, pivalate, propionate, pyruvate, salicylate, succinamate, succinate, and tropolonate.

16. A foam according to claim 1 wherein the anion is selected from the group consisting of (d) anions represented by the structure of the following formula:

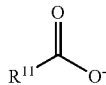

wherein R$^{11}$ is selected from the group consisting of:

(i) —CH$_3$, —C$_2$H$_5$, or a C$_3$ to C$_{10}$ straight-chain, branched or cyclic alkane or alkene group, optionally substituted with at least one member selected from the group consisting of Cl, Br, F, I, OH, NH$_2$ and SH;

(ii) —CH$_3$, —C$_2$H$_5$, or a C$_3$ to C$_{10}$ straight-chain, branched or cyclic alkane or alkene group comprising one to three heteroatoms selected from the group consisting of O, N, Si and S, and optionally substituted with at least one member selected, from the group consisting of Cl, Br, F, I, OH, NH$_2$ and SH;

(iii) a C$_6$ to C$_{10}$ unsubstituted aryl, or C$_6$ to C$_{10}$ unsubstituted heteroaryl, group having one to three heteroatoms independently selected from the group consisting of O, N, Si and S; and (iv) a C$_6$ to C$_{10}$ substituted aryl, or C$_6$ to C$_{10}$ substituted heteroaryl, group having one to three heteroatoms independently selected from the group consisting of O, N, Si and S; and wherein said substituted aryl or substituted heteroaryl group has one to three substituents independently selected from the group consisting of:

(A) —CH$_3$, —C$_2$H$_5$, or a C$_3$ to C$_{10}$ straight-chain, branched or cyclic alkane or alkene group, optionally substituted with at least one member selected from the group consisting of Cl, Br, F, I, OH, NH$_2$ and SH, (B) OH, (C) NH$_2$, and (D) SH.

17. A metastable liquid that comprises a fluorocarbon blowing agent and an ionic compound, wherein the ionic compound comprises an anion selected, from the group consisting of [BF$_4$]$^-$, [PF$_6$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$], [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

18. A liquid according to claim 17 wherein a blowing agent is selected from the group consisting of hydrofluorocarbons and fluoro-olefins.

19. A liquid according to claim 17 wherein a blowing agent is selected from the group consisting of tetrafluoromethane (Freon 14), fluoroform (Freon 23), hexafluoroethane (Freon 116), difluoromethane (HFC-32), 1,1-difluoroethane, 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a), fluoroethane (HFC-161), pentafluoroethane (HFC-125), 1,1,1,3,3-pentafluoropropane (HFC-245fa), 1,1,1,3,3-pentafluorobutane (HFC-365mfc), 2,3,3,3-tetrafluoroprop-1-ene (HFO-1234yf), and mixtures thereof.

\* \* \* \* \*